United States Patent
Sim et al.

(10) Patent No.: US 10,041,028 B2
(45) Date of Patent: Aug. 7, 2018

(54) PHOTOBIOREACTOR MADE OF A TRANSPARENT FILM

(75) Inventors: Sang Jun Sim, Seoul (KR); Eun Hye Kim, Gyeonggi-do (KR)

(73) Assignee: Sungkyunkwan University Foundation for Corporation Collaboration, Suwon-si, Gyeonggi-do (KR)

( * ) Notice: Subject to any disclaimer, the term of this patent is extended or adjusted under 35 U.S.C. 154(b) by 677 days.

(21) Appl. No.: 13/995,768

(22) PCT Filed: Jan. 20, 2011

(86) PCT No.: PCT/KR2011/000412
§ 371 (c)(1),
(2), (4) Date: Jun. 19, 2013

(87) PCT Pub. No.: WO2011/090330
PCT Pub. Date: Jul. 28, 2011

(65) Prior Publication Data
US 2013/0309762 A1 Nov. 21, 2013

(30) Foreign Application Priority Data
Jan. 20, 2010 (KR) .................. 10-2010-0005212

(51) Int. Cl.
 *C12M 1/00* (2006.01)
(52) U.S. Cl.
 CPC .......... *C12M 21/02* (2013.01); *C12M 23/22* (2013.01); *C12M 23/14* (2013.01); *C12M 23/34* (2013.01)
(58) Field of Classification Search
 CPC ...... C12M 21/02; C12M 23/22; C12M 27/18; C12M 27/20; C12M 27/24; C12N 1/12; A01G 33/00
(Continued)

(56) References Cited

U.S. PATENT DOCUMENTS 3,955,317 A * 5/1976 Gudin .................. C12M 21/02
                                                             435/292.1
4,724,214 A    2/1988 Mori
(Continued)

FOREIGN PATENT DOCUMENTS

EP          0343885       * 11/1989
JP     2007-330215 A      12/2007
(Continued)

OTHER PUBLICATIONS

KR1020030018197 translation text and figures (dated Mar. 2003).*

*Primary Examiner* — William H. Beisner
(74) *Attorney, Agent, or Firm* — Rabin & Berdo, P.C.

(57) ABSTRACT

The present invention relates to a photobioreactor, and more particularly, a photobioreactor for culturing living organisms such as microalgae, which carry out photosynthesis using carbon dioxide and light energy. The photobioreactor includes: (a) a reaction vessel, in which photosynthesis occurs by photosynthetic organisms; (b) a multipurpose inlet/outlet formed at the outside upper end of the reaction vessel; (c) an outer pipe connected to the multipurpose inlet/outlet at the outside of the reaction vessel; and (d) an inner pipe connected to the multipurpose inlet/outlet at the inside of the reaction vessel, wherein the reaction vessel is made of a transparent film.

The photobioreactor according to the present invention is advantageous in that the reaction vessel in which photosynthesis occurs is a plate-type and made of a transparent film, thus achieving improved light transmittance and mobility, and enabling the economically advantageous manufacture and operation thereof. Therefore, the photobioreactor of the present invention can be easily installed anywhere carbon dioxide is discharged, such as around a power-generating plant, in an urban region, a farm, etc., to culture a variety of (Continued)

photosynthetic organisms, and thus to produce useful substances having economically high added values.

11 Claims, 6 Drawing Sheets

(58) Field of Classification Search
USPC ........................................................ 435/292.1
See application file for complete search history.

(56) References Cited

U.S. PATENT DOCUMENTS

| | | |
|---|---|---|
| 4,900,678 A | 2/1990 | Mori |
| 5,350,080 A * | 9/1994 | Brown ................ B67D 7/0288 215/247 |
| 5,576,211 A * | 11/1996 | Falkenberg ............ C12M 23/24 435/297.1 |
| 6,432,698 B1 * | 8/2002 | Gaugler et al. ............ 435/296.1 |
| 6,509,188 B1 | 1/2003 | Trösch et al. |
| 7,980,024 B2 | 7/2011 | Berzin et al. |
| 2005/0032211 A1 * | 2/2005 | Shaaltiel .................... 435/292.1 |
| 2006/0016708 A1 * | 1/2006 | Ingraham ................ A61J 1/10 206/439 |
| 2009/0130706 A1 | 5/2009 | Berzin et al. |
| 2010/0287829 A1 | 11/2010 | Bussell |

FOREIGN PATENT DOCUMENTS

| | | |
|---|---|---|
| KR | 10-1984-0003285 A | 8/1984 |
| KR | 10-2002-0008825 A | 1/2002 |
| KR | 10-0399977 B1 | 9/2003 |
| WO | WO 2009/094196 A2 | 7/2009 |

* cited by examiner

PHOTOBIOREACTOR MADE OF A TRANSPARENT FILM

TECHNICAL FIELD

The present invention relates to a photobioreactor, and more particularly, to a photobioreactor for culturing living organisms such as microalgae, which carry out photosynthesis using carbon dioxide and light energy.

BACKGROUND ART

Greenhouse gas has been emitted by the use of fossil fuel, thus causing global warming. Such global warming results in climate change and environmental change, and jeopardizes the survival of all organisms including humans. Therefore, many studies and developments for reducing carbon dioxide have been performed. As one method, a study has been conducted actively for recovery and biological conversion of carbon dioxide.

A study has been conducted actively for microalgae as photosynthetic organisms for the biological conversion of carbon dioxide. Phytoplankton microalgae use the sun as energy source, similarly to other photosynthetic organisms, and grow through photosynthesis for immobilizing carbon dioxide.

The reasons why microalgae draw attention as means for immobilizing carbon dioxide are as follows. First, since microalgae harness solar energy as a main energy source, similarly to carbon dioxide absorption in a plant, microalgae need only a small amount of energy for recovering carbon dioxide. Therefore, since the small amount of carbon dioxide is produced at the time of operation of immobilizing carbon dioxide, removal efficiency is high from the viewpoint of a carbon dioxide resin.

Second, microalgae have the immobilization rate of carbon dioxide higher than that of a plant, and a required site area is small. According to the findings of the Tokyo Electric Power Research Institute, the immobilization rate of microalgae is 2.8 times higher than the fastest growing sugar cane, and 15 times higher than of the most common species of pine in Korea.

In addition, there is no need for separation and concentration of carbon dioxide because carbon dioxide can be immobilized directly from combustion gas. In addition, microalgae which are produced during immobilization of carbon dioxide may be used as biological products because they contain various useful substances.

However, when the carbon dioxide-immobilization process using microalgae is performed by using the bioreactor which has been applied practically in industries, it is difficult to reduce energy and supply light energy for allowing microalgae to grow, due to high consumption of electrical energy.

Generally, an apparatus for culturing photosynthetic organisms for the purpose of carbon dioxide immobilization is usually divided into an open-type culture apparatus for outdoor mass culture and a close-type photobioreactor having a small volume. In the case of the open-type outdoor culture apparatus, it was usually used in a form such as a lake or a large pond in Germany, Japan or U.S. However, since the open-type outdoor mass culture apparatus in a form of a pond should be manufactured by an expensive reinforced concrete structure, a lot of energy is consumed at the time of consecutive stirring, and pollution prevention, and separation and purification of cultured microalgae are difficult. Furthermore, in the case of the mass culture apparatus, it has slow growth rate of photosynthetic organisms and low growth yield because generally light is not effectively transferred to the inner portion.

Presently, the developed close-type photobioreactor includes a general stirring type reactor, a plate-type reactor, a tube-type reactor, and a column-type reactor, and the like. It could be expected that the close-type reactor has a cell growth rate higher than that of the outdoor mass culture apparatus, and it is easy to control operation conditions. However, the close-type reactor has a high initial cost and a high operation management cost, and it is difficult to use efficiently light energy as a crucial factor of a photobioreactor. In order to use light energy, a reactor in which a light source is installed in the reactor was developed. However, the reactor has good light efficiency, but it is not efficient because electrical energy of artificial fluorescent lamp or LED is used. In addition, since the close-type reactor is generally manufactured by a reinforced glass or acryl which is stationary, it is difficult to perform mass culture and clean the reactor, and indoor space cannot be employed effectively.

The present inventors found that, when a reaction vessel where photosynthesis occurs is made of a transparent film, instead of a reinforced glass or acryl that has been generally used, the reaction vessel has good light transmittance, thus enabling microalgae to grow well, and the reaction vessel has good mobility because it is light, thus enabling the economically advantageous manufacture and operation thereof. Also, the present inventors found that, when the inner space of a photobioreactor made of a transparent film is partially partitioned, carbon dioxide and photosynthetic organisms are further dispersed therein and reduction of light transmittance caused by the deformation of the reactor may be prevented. The present invention was accomplished.

DISCLOSURE OF INVENTION

Technical Problem

An object of the present invention is to provide an economical photobioreactor which has low consumption of energy and has a structure capable of obtaining sufficient light energy at the time of operation of the reactor, compared to a bioreactor such as a stirring type reactor or a plate-type reactor, which has been widely spread.

Another object of the present invention is to provide a photobioreactor capable of a simplified manufacture and operation, and good mobility.

Technical Solution

The photobioreactor according to the present invention is advantageous in that the reaction vessel in which photosynthesis occurs is a plate-type and made of a transparent film, thus achieving improved light transmittance and mobility, and enabling the economically advantageous manufacture and operation thereof. The photobioreactor does not have the flat bottom portion thereof, but has a structure in which the grooves in the "V" shape are consecutively formed. Therefore, culture solution may be mixed by gas such as carbon dioxide or gas without a stirrer such as a magnetic bar, an impeller, or the like.

Since the inner space of the reactor is partially partitioned, carbon dioxide and photosynthetic organisms may be further dispersed therein and reduction of light transmittance caused by deformation of the reactor may be prevented. Therefore, the photobioreactor of the present invention can be easily installed anywhere carbon dioxide is discharged, such as around a power-generating plant, in an urban region, a farm, etc., to culture a variety of photosynthetic organisms, thereby making it possible to produce useful substances having economically high added value.

DETAILED DESCRIPTION OF MAIN ELEMENTS

Figure 1:
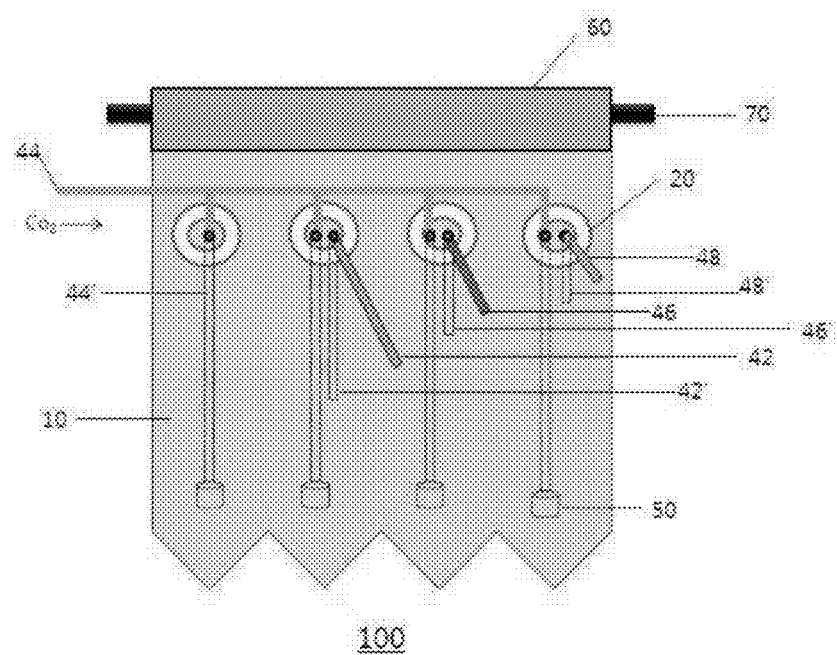
FIG. 1 shows the structure of a photobioreactor according to an exemplary embodiment of the present invention.

10: Reaction vessel
20: Multipurpose inlet/outlet
21: Nut type circular fixing pin
23: Bolt type circular fixing pin
24: Fixing connection portion
25: Stopping rubber
26: Fixing connection portion cap
32: Injection hole of photosynthetic organism and culture solution
34: Injection hole of carbon dioxide-containing gas
36: Extraction hole of specimen sample
38: Discharge hole for gas
42: Outer pipe for injecting photosynthetic organism and culture solution
42': Inner pipe for injecting photosynthetic organism and culture solution
44: Outer pipe for injecting carbon dioxide-containing gas
44': Inner pipe for injecting carbon dioxide-containing gas
46: Outer pipe for extracting specimen sample
46': Inner pipe for extracting specimen sample
48: Outer pipe for discharging gas
48': Inner pipe for discharging gas
50: Sprayer
60: Hanging portion
70: Support bar
80: Corrugated partition Best Mode for Carrying out the Invention The present invention is to confirm that even though a plate-type photobioreactor is manufactured by using a reaction vessel in which photosynthesis occurs, made of a transparent film instead of a reinforced glass or acryl that has been used generally, the photobioreactor has good light transmittance.

In the present invention, a photobioreactor including a plate-type reaction vessel which is made of a transparent film was subjected to culturing microalgae. As a result, it was confirmed that the photobioreactor has good light transmittance.

In other words, in an exemplary embodiment of the present invention, a plate-type photobioreactor which includes a reaction vessel made of a low density polyethylene (LDPE) film, and a mixed film (PET+CPP) of polyethylene terephthalate and non-stretched polypropylene is manufactured, and then *Haematococcus pluvialis* microalgae is cultured. As a result, it could be confirmed that the plate-type photobioreactor has good light transmittance, in which microalgae grow well.

Therefore, in one aspect of the present invention, there is provided a photobioreactor, including: (a) a reaction vessel, in which photosynthesis occurs by photosynthetic organisms; (b) a multipurpose inlet/outlet formed at the outside upper end of the reaction vessel; (c) an outer pipe connected to the multipurpose inlet/outlet at the outside of the reaction vessel; and (d) an inner pipe connected to the multipurpose inlet/outlet at the inside of the reaction vessel, wherein the reaction vessel is made of a transparent film.

Hereinafter, a photobioreactor according to the present invention will be described with reference to the drawings.

FIG. 1 shows the structure of a photobioreactor 100 according to an exemplary embodiment of the present invention.

As shown in FIG. 1, the reaction vessel 10 is made of a transparent film, and includes, at the upper portion thereof, a hanging portion 60 so as to support or fix the reaction vessel. The hanging portion 60 is hollow such that a support bar 70 may be inserted thereinto. The support bar 70 is provided to support the photobioreactor, and it is not specifically limited as long as the photobioreactor has strength that may support a weight of the photobioreactor. Both ends of the support bar 70 may be hung by a separate stand or the like.

The transparent film is not specifically limited as long as it is transparent and has good light transmittance such that photosynthetic organisms may grow easily. The transparent film includes (a) low density polyethylene (LDPE), (b) a mixed film of polyethylene terephthalate and non-stretched polypropylene (PET+CPP), (c) polyacetal (POM), (d) polycarbonate (PC), (e) polyester sulfone (PES), (f) polyethylene (PE), (g) polyvinyl chloride (PVC), (h) polyethylene terephthalate (PET), (i) polypropylene (PP), and (j) polyphenylene oxide (PPO=PPE). The transparent film is light and transparent, and has good mechanical strength, as well as the same light transmittance, compared to glass or acryl that has been widely used for a reaction vessel of a photobioreactor.

The reaction vessel 10 constituting the photobioreactor according to the present invention may be a plate-type and a bubble column-type when culture solution is injected. Since the reaction vessel is a plate-type, it has good light transmittance because of a small distance of transmitted light in the reactor.

Figure 2:
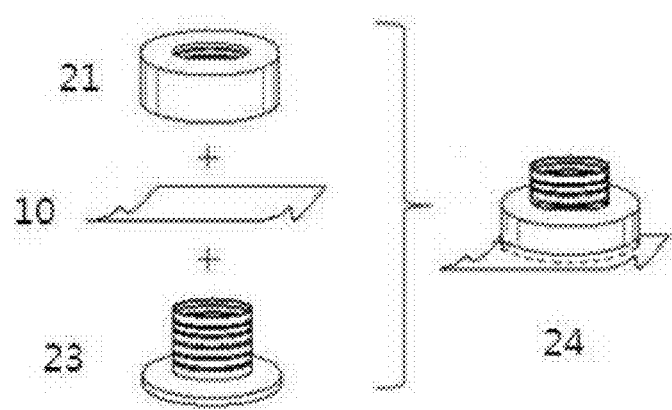
FIG. 2 illustrates a combination of a fixing connection portion of a multipurpose inlet/outlet according to an exemplary embodiment of the present invention.

The multipurpose inlet/outlet 20 is attached detachably at the outside upper end of the reaction vessel 10. FIG. 2 illustrates a combination of a fixing connection portion of a multipurpose inlet/outlet according to an exemplary embodiment of the present invention. As shown in FIG. 2, the fixing connection portion 24 disposed inside and outside the reaction vessel 10 includes a nut type circular fixing pin 21 disposed outside the reaction vessel and a bolt type circular fixing pin 23 disposed inside the reaction vessel.

Figure 3:
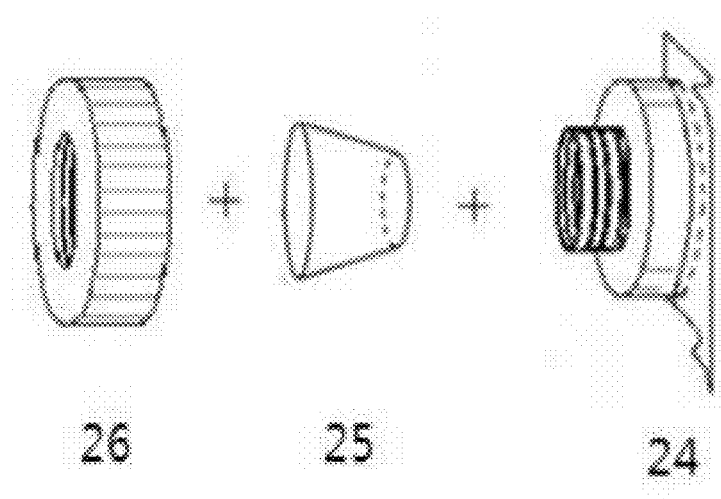
FIG. 3 shows a combination example of a multipurpose inlet/outlet according to an exemplary embodiment of the present invention.

FIG. 3 shows a combination example of a multipurpose inlet/outlet according to an exemplary embodiment of the present invention. As shown in FIG. 3, a fixing connection portion cap 26 and the fixing connection portion 24 may be combined with each other using bolt type and nut type screws. At the time of combining the fixing connection portion cap 26 and fixing connection portion 24 with each other, a stopping rubber 25 may be combined therebetween for prevention of pollution by outer microorganisms or organisms. The stopping rubber may include holes such that an outer pipe and an inner pipe may be inserted thereinto.

The multipurpose inlet/outlet 20 includes a hole for carrying out a function selected from the group consisting of (a) injecting a photosynthetic organisms and culture solution, (b) injecting a carbon dioxide-containing gas, (c) extracting a specimen sample and (d) discharging gas. The number of holes is not specifically limited.

Figure 4:
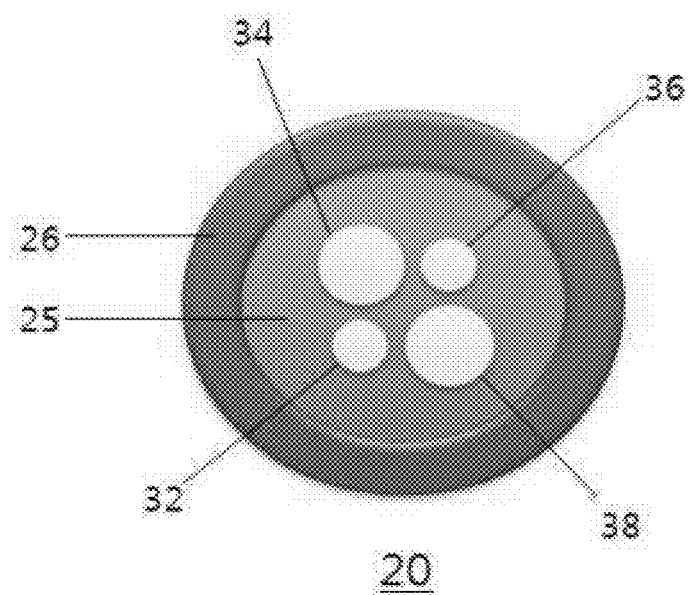
FIG. 4 shows a multipurpose inlet/outlet formed in a photobioreactor according to an exemplary embodiment of the present invention.

FIG. 4 shows a multipurpose inlet/outlet formed in a photobioreactor according to an exemplary embodiment of the present invention. As shown in FIG. 4, the stopping rubber 25 of the multipurpose inlet/outlet 20 may include an injection hole 32 of photosynthetic organisms and culture solution, an injection hole 34 of a carbon dioxide-containing gas, an extraction hole 36 of a specimen sample, or a discharge hole 38 for gas.

The holes are formed in the multipurpose inlet/outlet 20 such that outer pipes 42, 44, 46 and 48 disposed outside the reaction vessel may be connected to inner pipes 42', 44', 46' and 48' disposed inside the reaction vessel, respectively. More specifically, the outer pipe includes an outer pipe 42 for injecting photosynthetic organisms and culture solution, an outer pipe 44 for injecting a carbon dioxide-containing gas, an outer pipe 46 for extracting a specimen sample and an outer pipe 48 for discharging gas. The inner pipe includes an inner pipe 42' for forming an injection hole for injecting photosynthetic organisms and culture solution, an inner pipe 44' for injecting a carbon dioxide-containing gas, an inner pipe 46' for extracting a specimen sample and an inner pipe 48' for discharging gas.

The outer pipe and inner pipe are not specifically limited as long as they may have a hole in a hose shape, and include a stainless steel hose or a silicon hose, which is sterilizable. In addition, the outer pipe and the inner pipe are integrally formed therewith or may be connected to the multipurpose inlet/outlet 20, respectively.

The outer pipe 48 for discharging gas which is connected to the discharge hole 38 for gas is allowed to discharge gas and unabsorbable carbon dioxide to the outside of the reactor. The outer pipe 46 for extracting a specimen sample which is connected to the extraction hole 36 of the specimen sample is allowed to extract a specimen at the time of operation of the photobioreactor 100. At the time of extracting the specimen sample, the outer pipe 46 for the extraction may further include a close valve (not shown) such that pollution substances are not introduced into the reactor.

The outer pipe 44 for injecting carbon dioxide-containing gas which is connected to the injection hole 34 for gas including carbon dioxide-containing gas is allowed to supply carbon dioxide to the photobioreactor 100. Then, a feed rate of carbon dioxide may be controlled through a flow meter that is separately provided outside the photobioreactor. A carbon dioxide distribution may be varied depending on a size or properties of the photosynthesis organisms, internal size of the reactor, and properties of a sprayer, in the photobioreactor 100. Thus, a feed rate of carbon dioxide may be controlled using the flow meter.

The number of multipurpose inlets/outlets 20 installed may depend on the volume of the photobioreactor 100.

A sprayer 50 for dispersing carbon dioxide in the photobioreactor is attached to the end of the inner pipe 44' for injecting the carbon dioxide-containing gas in the inner pipe. The sprayer 50 serves to help to disperse photosynthesis organisms in the reactor.

The sprayer 50 is not limited to a cylindrical type, a polygonal type, or a spherical type as long as it enables air to be injected.

Furthermore, in the present invention, when the lower portion of the reactor is manufactured to have corrugation instead of a flat surface, it was expected that a space (i.e., dead zone) where cells are not mixed by gravity and accumulated space (dead zone) is reduced, and thus the culture solution may be mixed easily.

In another exemplary embodiment of the present invention, as shown in FIG. 1, the reaction vessel is manufactured such that the lower portion thereof where a sprayer is located includes a groove in a "V" shape, in which microalgae *Haematococcus pluvialis* are cultured. Therefore, it could be confirmed that culture solution is mixed homogenously without a stirrer.

Therefore, the reaction vessel is manufactured such that the lower portion where the sprayer is located includes a groove in a "V" shape. The groove in a "V" shape may be formed such that the number of grooves in the "V" shape is the same as the number of sprayers. The number of sprayers or the number of grooves in the "V" shape may be selected optionally, i.e., 1 to 100, and preferably 1 to 10.

The groove in the "V" shape has an internal angle of 30 to 160°. When the internal angle of the groove in the "V" shape is less than 30°, the interval of the partition portion of the reactor is reduced, or the groove portion in the "V" shape is increased significantly. When the internal angle of the groove in the "V" shape is larger than 160°, the groove in the "V" shape may not be formed. The maximum internal interval of the groove in the "V" shape may be suitably selected, without limitation, depending on the volume of the reactor, the diameter of a carbon dioxide sprayer to be used, or the like. For example, when a carbon dioxide sprayer having a diameter of 1.2 cm is used in the reactor having a volume of 3 to 8 L, the groove in the "V" shape may have the maximum internal interval of 3 to 30 cm. When the volume of the reactor or the size of a carbon dioxide sprayer is increased, the maximum internal interval of the groove in the "V" shape may be also increased.

The photobioreactor 100 according to the present invention has a structure such that the lower portion of the reaction vessel 10 where the sprayer 50 is located includes a groove in the "V" shape, and photosynthetic organisms are collected at the edge of the groove in the "V" shape, and therefore culture solution may be mixed by gas such as carbon dioxide or gas without a stirrer such as a magnetic bar, an impeller, or the like.

The photobioreactor 100 according to the present invention has a height of 20 to 500 cm, and preferably 40 to 200 cm, a width length of 3 to 1500 cm, and a side surface length (i.e., a depth of reactor) of 2 to 15 cm. The term "side surface length" means a depth when culture solution is injected to the photobioreactor.

On the other hand, the present inventors found that a plate-type photobioreactor is manufactured using a reaction vessel where photosynthesis occurs, made of a transparent film, instead of a reinforced glass, or acryl that has been used generally. Herein, when the inner space of a photobioreactor is partially partitioned, carbon dioxide and photosynthetic organisms are further dispersed therein and reduction of light transmittance caused by the deformation of the reactor may be prevented.

In the present invention, the photobioreactor including a reaction vessel, made of a transparent film, in which the inner space is partially partitioned, was subjected to culturing microalgae. As a result, it was confirmed that the photobioreactor has good light transmittance.

Therefore, in another aspect of the present invention, there is provided a photobioreactor, including: (a) a reaction vessel made of a transparent film, in which photosynthesis occurs by photosynthetic organisms; (b) a multipurpose inlet/outlet formed at the outside upper end of the reaction vessel; (c) an outer pipe connected to the multipurpose inlet/outlet at the outside of the reaction vessel; and (d) an inner pipe connected to the multipurpose inlet/outlet at the inside of the reaction vessel, wherein the inner space of the reaction vessel is partially partitioned.

Figure 5:
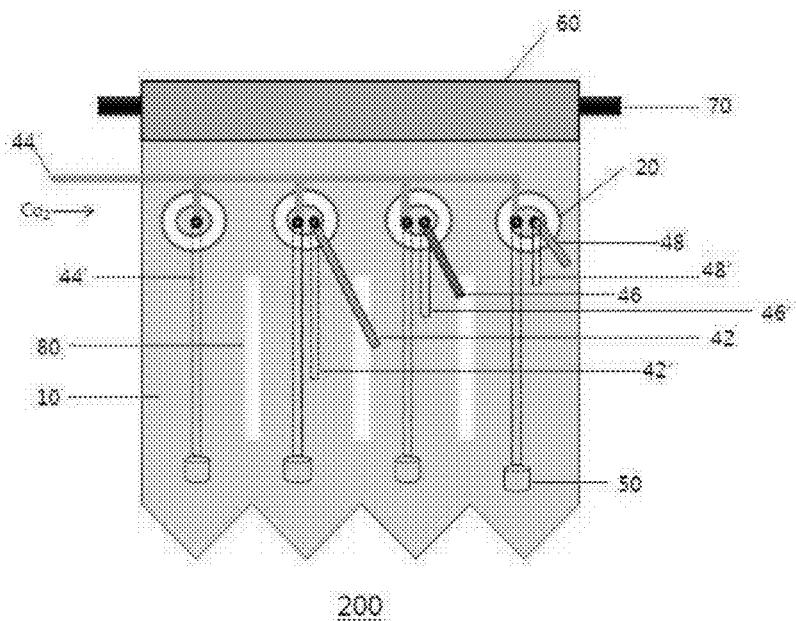
FIG. 5 shows the structure of a photobioreactor in which the inner space is partially partitioned according to an exemplary embodiment of the present invention.
Figure 6:
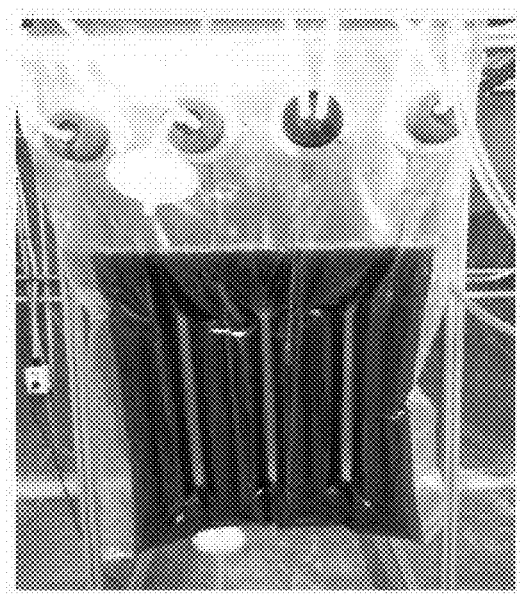
FIG. 6 is a photograph showing one example of a photobioreactor according to an exemplary embodiment of the present invention.
Figure 7:
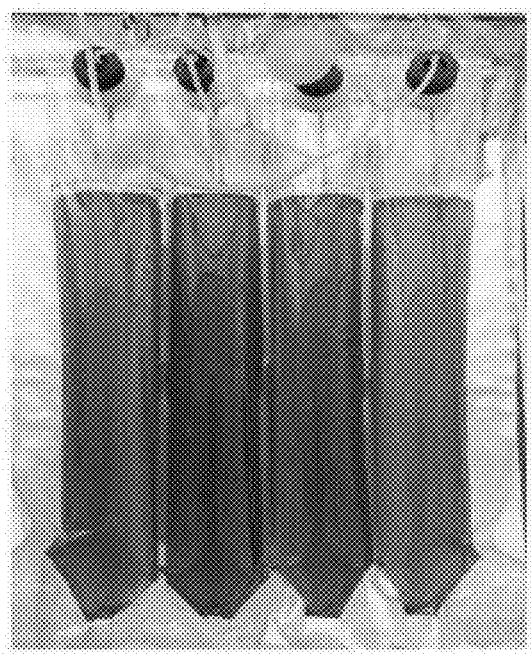
FIG. 7 is a photograph showing one example of a photobioreactor according to an exemplary embodiment of the present invention.

FIGS. 5 to 7 show the structure of a photobioreactor 200 in which the inner space is partially partitioned according to an exemplary embodiment of the present invention.

As shown in FIG. 5, the inner space of the reaction vessel 10 is partially partitioned by attaching predetermined portions inside the front and rear surfaces of the reaction vessel to each other in a vertical line shape to form a corrugated partition 80. Since the reaction vessel 10 is made of a transparent film, when the predetermined portions inside the reaction vessel are attached to each other in a vertical line shape, the inner space may be partitioned.

In the present invention, the inner space was partially partitioned. It means that the inner space of the reaction vessel is partitioned in a vertical line shape, the inner space was not partitioned from the top to the bottom of the reaction vessel, but a certain interval is spaced apart from both the top and the bottom, and the inner space was partitioned. Therefore, culture solution in the reaction vessel may be transferred through a path spaced apart by a certain interval.

The corrugated partition may be formed between the multipurpose inlet/outlet and the bottom of the reaction vessel. The length of the corrugated partition may be varied depending on the height of the reactor. When the length of the corrugated partition, that is, the surface where the front surface of the reaction vessel is attached to the inside of the rear surface thereof is too short, a partition effect cannot be obtained. When the length is too long, carbon dioxide and photosynthetic organisms in the inner space of the reactor may hardly obtain homogeneous distribution.

The interval of the partition, that is, a distance between corrugated partition and subsequent corrugated partition may be selected suitably without limitation depending on the volume of the reactor, or the diameter of a carbon dioxide sprayer to be used, as described above.

As described above, the photobioreactor where the inner space is partially partitioned is formed such that the lower portion of the reaction vessel where a sprayer is located includes a groove in the "V" shape.

EXAMPLES

Hereinafter, the present invention will be described in detail with reference to the Examples. The Examples include one example of the present invention, and are not to be construed as limiting a scope of the present invention, which is evident to those skilled in the art.

Particularly, the Examples were subjected to culturing *Chlorella vulgaris* and *Haematococcus pluvialis* among microalgae in the photobioreactor according to the present invention. However, it is evident to those skilled in the art that other microalgae are allowed to be cultured.

Example 1

Measure of Light Transmittance in Photobioreactor Made of Transparent Film

A photobioreactor of FIG. 1 (height: 40 cm, width length: 45 cm, side surface length: 5 cm, volume: 6 l, maximum internal interval of a groove of "V" shape: 15 cm*3) was manufactured by using a low density polyethylene film (LDPE) and a mixed film of polyethylene terephthalate and non-stretched polypropylene (PET+CPP, Filmax, CPP Film), respectively.

In the manufactured photobioreactor, *Haematococcus pluvialis* (NIES-144) provided from MCC-NIES (Microbial Culture Collection, National Institute of Environmental Studies (NIES), Japan) was cultured under conditions (culture temperature: 23~25, culture time: 150 hours, pH: 7.5) at a concentration of 0.33 g/L in the NIES medium in which a carbon source is removed (NIES-C). During the culture, distance was measured in accordance with a light flux (360 μ mol photon $m^{-2}s^{-1}$) with the same intensity. A result was shown in FIG. 8.

Figure 8:
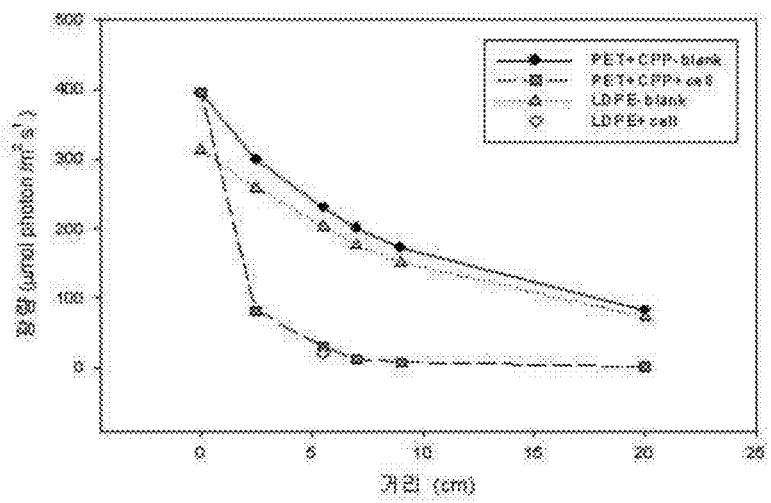
FIG. 8 is a graph showing a relationship between an inner distance (side surface length) of a reactor and a light flux, in accordance with materials of a photobioreactor according to an exemplary embodiment of the present invention.

As shown in FIG. 8, the photobioreactor made of LDPE has light transmittance lower than the photobioreactor made of PET+CPP as translucent materials, but light transmittance of each reactor was measured when 0.33 g/L of *Haematococcus pluvialis* cell was injected to two reactors. Then, it was believed that two reactors have the similar light transmittance from each other.

Example 2

Measure of Cell Culture in Accordance with Photobioreactor

A NIES medium (NIES-C) was added to a reactor which has a material (PET+CPP), a height, a width length, and a side surface length which are the same as the photobioreactor manufactured in Example 1 except that a groove in the "V" shape is not formed in the lower portion of the reactor, and the reactor manufactured in Example 1, *Haematococcus pluvialis* (NIES-144) were inoculated, followed by culturing for 2 days under the same conditions, and then the state of the cells was observed. A result was shown in Table 1.

TABLE 1

| Carbon dioxide VVM | Groove in the V shape | No groove in the V shape |
|---|---|---|
| 0.05 | X | X |
| 0.1 | X | X |
| 0.15 | Δ | X |
| 0.2 | ○ | X |
| 0.25 | ○ | Δ |
| 0.3 | ○ | Δ |
| 0.35 | ○ | ○ |
| 0.4 | Δ | ○ |
| 0.45 | X | ○ |
| 0.5 | X | Δ |
| 0.55 | X | X |

X: cell aggregation,
Δ: partial aggregation of cells (about 20~50%),
○: well stirred state As shown in Table 1, when a groove in the "V" shape was formed in a lower portion of the photobioreactor, followed by sparging with a small amount of carbon dioxide mixed gas, the photobioreactor was stirred homogeneously without aggregation of cells. However, when the photobioreactor of which the lower portion is flat was sparged with a small amount of carbon dioxide, it could be confirmed that cells were aggregated. Therefore, when the photobioreactor is used of which a groove in the "V" shape is formed in the lower portion, the feed rate of carbon dioxide may be reduced, and thus microalgae can be cultured economically.

Example 3

Analysis of Produced Astaxanthin from *Haematococcus Pluvialis*

*Haematococcus pluvialis* (NIES-144) and a NIES-C medium of Table 2 were added to the photobioreactor (made of LDPE) manufactured in Example 1 and a cylindrical photobioreactor (KBT, including a stirrer) made of glass, followed by culturing. Then, an initial inoculation density was 10% by volume, a culture temperature was 23 to 25, pH was 7.5, a light intensity was 80 µmol photon $m^{-2}s^{-1}$, a light period was 24 L:0 D, and a feed rate of carbon dioxide was 20 mL/min. The amount of astaxanthin extracted from *Haematococcus pluvialis* was measured in accordance with culture time. A result was shown in FIG. 9.

Figure 9:
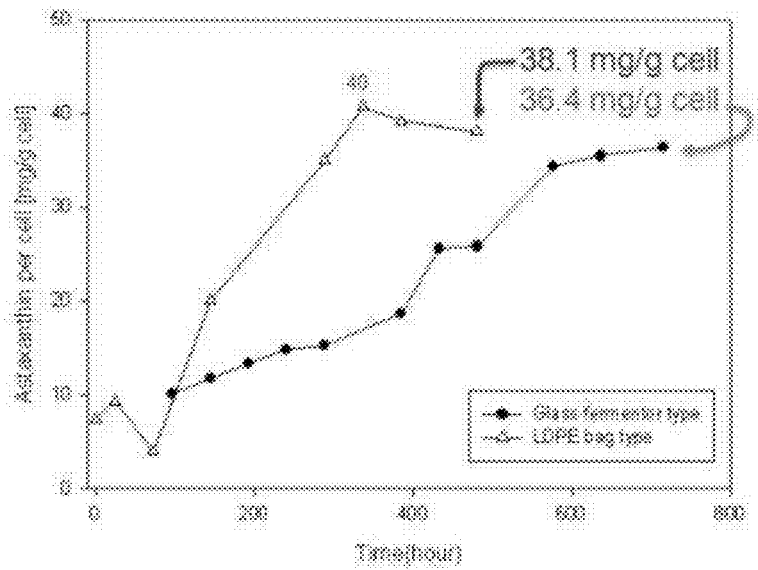
FIG. 9 is a graph showing the amount of astaxanthin to be produced in a photobioreactor according to an exemplary embodiment of the present invention and a general cylindrical stirring type reactor.

As shown in FIG. 9, when *Haematococcus pluvialis* were cultured in the photobioreactor made of LDPE, it was confirmed that the photobioreactor made of LDPE produces astaxanthin more than that of a cylindrical photobioreactor made of glass.

TABLE 2

| Component | content ($L^{-1}$) |
|---|---|
| Ca(NO$_3$)$_2$ | 0.15 g |
| KNO$_3$ | 0.10 g |
| Na$_2$ Glycerophosphate•5H$_2$O | 0.05 g |
| MgSO$_4$•7H$_2$O | 0.04 g |
| Tris-aminomethane | 0.50 g |
| Thiamine | 0.01 mg |
| Biotin | 0.10 µg |
| Vitamin B$_{12}$ | 0.01 µg |
| PIV metal solution (per liter) | 3 mL(Na$_2$EDTA; 1 g, FeCl$_3$ 6H$_2$O; 0.196 g, MnCl$_2$•4H$_2$O; 0.036 g, ZnSO$_4$•7H$_2$O; 0.022 g, CoCl$_2$•6H$_2$O; 4 mg, Na$_2$MoO$_4$•2H$_2$O; 2.5 mg) |

Example 4

Microalgae Culture Using Photobioreactor where Inner Space of Reaction Vessel is Partially Partitioned 4-1: *Haematococcus pluvialis* Culture A photobioreactor of FIG. 5 (height: 60 cm, width length: 45 cm, side surface length: 5 cm, volume: 6 l, corrugated partition length: 25 cm, partition interval: 15 cm*3) in which the inner space was partially partitioned was manufactured by using a low density polyethylene film (LDPE).

*Haematococcus pluvialis* (NIES-144) and a NIES-C medium of Table 2 were added to the manufactured photobioreactor (made of LDPE) and a photobioreactor (made of LDPE) which is the same as described above except that a partial partition was not formed, followed by culturing. Then, an initial inoculation density was 10% by volume, a culture temperature was 23 to 25, pH was 7.5, a light intensity was 80 µmol photon $m^{-2}s^{-1}$, a light period was 24 L:0 D, and a feed rate of carbon dioxide was 20 mL/min. The culture was carried out by changing a diameter of a sprayer for feeding the carbon dioxide and a feed rate of carbon dioxide so as to culture actively in the reactor, and then light transmittance was measured. Therefore, a result was shown in Table 3.

TABLE 3

| | Partially partitioned reactor | Reactor in which the inner space is not partially partitioned |
|---|---|---|
| Carbon dixodie sprayer | Sprayer diameter (1.2 cm) | Including hole in a pipe having a length of 15 cm or more, so as to reach 80% of a width length of reactor |
| Feed rate of carbon dioxide for homogeneous stirring | about 0.2 VVM | 0.5 VVM or more |
| Light transmittance (depth of reactor) | good (side surface length of 2~10 cm) | bad (side surface length of 15 cm or more) |

As shown in Table 3, even though a carbon dioxide sprayer having a small diameter is used in a partially partitioned reactor and a feed rate of carbon dioxide is about 0.2 VVM, *Haematococcus pluvialis* is stirred and cultured actively. Also, since the reactor is partially partitioned, the depth thereof is not increased, and therefore light transmittance is good. Whereas, in the case of the reactor which is not partially partitioned, the reactor includes a hole in a pipe having a length of 15 to 36 cm, so as to reach 80% of a width length, and thus it could be confirmed that, when 0.5 VVM or more carbon dioxide is injected, *Haematococcus pluvialis* is stirred. In addition, when culture solution is injected into the reactor which is not partially partitioned, it could be confirmed that a depth thereof is increased significantly and light transmittance is degraded.

4-2: *Chlorella* Culture

A photobioreactor of FIG. 5 (height: 80 cm, width length: 60 cm, side surface length: 5 cm, volume: 15 l, length of corrugated partition: 25 cm, partition interval: 15 cm*3) in which the inner space is partially partitioned, was manufactured by using a mixed film of polyethylene terephthalate and non-stretched polypropylene (PET+CPP, manufactured by Filmax, CPP Film), respectively.

*Chlorella vulgaris* (AG10034) and TAP-C medium (medium removing a carbon source from TAP medium) with the composition of Table 4 were injected into the manufactured photobioreactor, followed by culturing. A result was shown in FIG. 10. Then, an initial inoculation density was 10% by volume, a culture temperature was 23, pH was 7.0, a light intensity was 0~300 μmol photon $m^{-2}s^{-1}$, a light period was 11 L:13 D (i.e., natural sunlight due to outdoor culture), and a feed rate of carbon dioxide was 0.1 VVM. A control cultured *chlorella* in the same condition except that the photobioreactor was changed to 250 mL of an Erlenmeyer flask.

Figure 10:
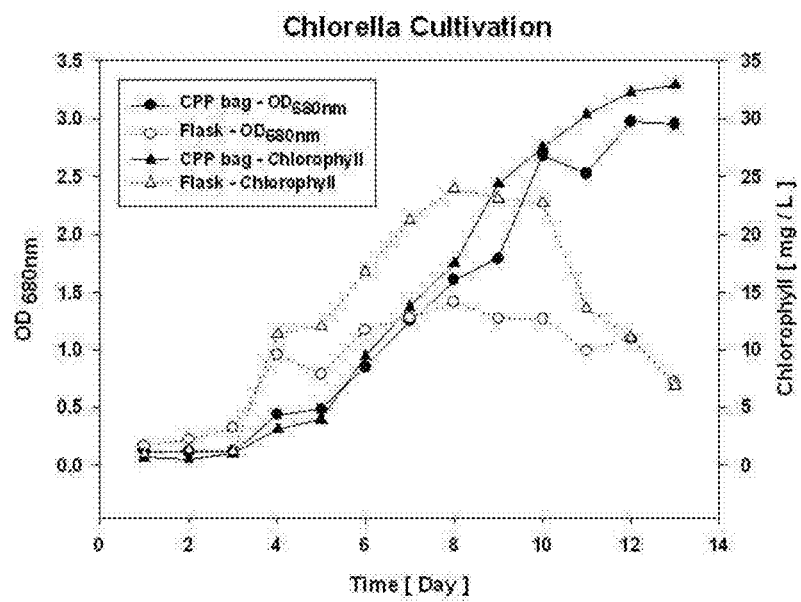
FIG. 10 is a graph showing the result of *chlorella* culture in a photobioreactor according to an exemplary embodiment of the present invention and an Erlenmeyer flask.

As shown in FIG. 10, it could be confirmed that the amount of *chlorella* cultured in a partially partitioned photobioreactor is increased continuously until 14 days, and the amount of chlorophyll extracted from *chlorella* is increased, whereas the amount of cultured *chlorella* and chlorophyll in the Erlenmeyer flask is increased gradually until 8 days, and then is decreased.

TABLE 4

| Stock Solution | For 1 L |
| --- | --- |
| 1M Tris base | 20 ml |
| Phosphate Buffer | 1 ml |
| Hutner's Trace metals | 1 ml |
| Nutrient stock | 10 ml |

Experimental Example 1

Measure of Light Transmittance in Accordance with Depth of Photobioreactor

*Haematococcus pluvialis* were cultured in the same method except that the depth of the photobioreactor manufactured in Example 4-1 was changed. A result was shown in FIG. 11.

Figure 11:
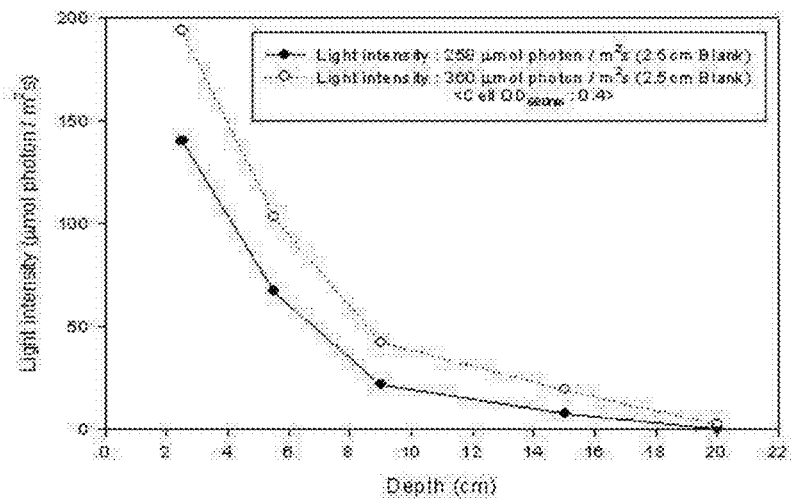
FIG. 11 is a graph measuring light transmittance in accordance with the depth of a photobioreactor according to an exemplary embodiment of the present invention.

As shown in FIG. 11, it could be confirmed that, when the light of the certain intensity is transmitted to the reactor, a depth thereof is increased and light transmittance is decreased.

Experimental Example 2

Measure of Light Transmittance of Photobioreactor in Accordance with Materials

*Haematococcus pluvialis* (NIES-144) and a NIES-C medium were added to the photobioreactor (made of LDPE) manufactured in Example 4-1 and a cylindrical photobioreactor (KBT, including a stirrer) made of glass, followed by culturing. During the culture, an initial inoculation density was 10% by volume, a culture temperature was 23 to 25, pH was 7.5, a light intensity was 80 μmol photon $m^{-2}s^{-1}$, a light period was 24 L:0 D, and feed rate of carbon dioxide was 20 mL/min. During the culture, distance in accordance with a light flux of the same intensity (258 and 360 μmol photon $m^{-2}s^{-1}$) was measured, respectively. A result was shown in FIG. 12.

Figure 12:
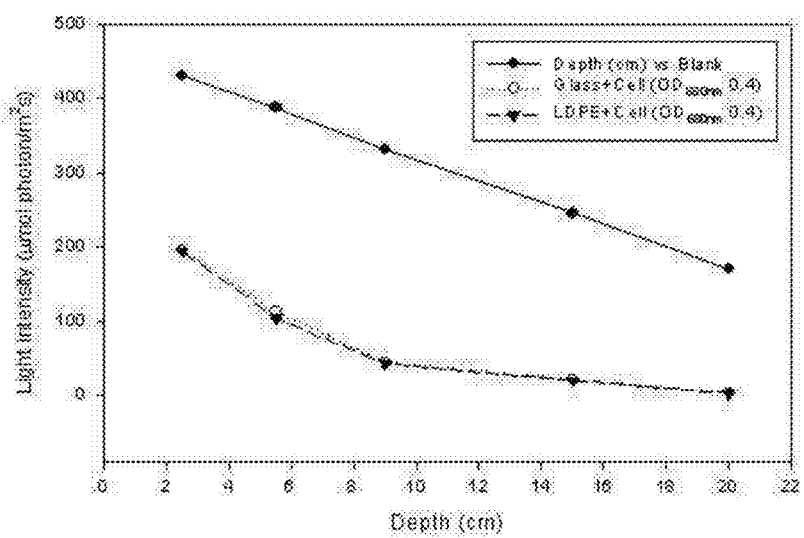
FIG. 12 is a graph showing a relationship between an inner distance (side surface length) of a reactor and a light flux, in accordance with materials of a photobioreactor according to an exemplary embodiment of the present invention and materials of a general cylindrical stirring type reactor.

As shown in FIG. 12, it was confirmed that the photobioreactor made of LDPE has the same light transmittance as that of a photobioreactor made of glass.

Example 5

Microalgae Culture Using Photobioreactor where Inner Space is Partially Partitioned Each photobioreactor which the inner space is partially partitioned, of FIG. 5 ((a) height: 60 cm, width length:45 cm, side surface length: 5 cm, volume: 6 l, length of corrugated partition: 25 cm, partition interval: 15 cm*3; (b) height: 60 cm, width length:30 cm, side surface length: 4 cm, volume: 4.5 l, length of corrugated partition: 25 cm, partition interval: 10 cm*3; (c) height: 60 cm, width length: 50 cm, side surface length: 15 cm, volume:8 L, length of corrugated partition: 25 cm, partition interval: 25 cm*2) was manufactured by using a mixed film of polyethylene terephthalate and non-stretched polypropylene (PET+CPP, manufactured by Filmax, CPP Film), in order to confirm a culture effect in accordance with partition interval.

*Haematococcus pluvialis* (NIES-144) was cultured in the photobioreactor manufactured in the same conditions as Example 4-1. A result was shown in Table 5.

TABLE 5

| Carbon dioxide VVM (sprayer diameter of 1.2 cm) | Reactor having partition interval of 10 cm | Reactor having partition interval of 15 cm | Reactor having partition interval of 25 cm |
| --- | --- | --- | --- |
| 0.1 | X | X | X |
| 0.2 | X | X | X |
| 0.25 | Δ | Δ | X |
| 0.3 | ○ | Δ | X |
| 0.35 | ○ | ○ | X |
| 0.4 | Δ | ○ | X |
| 0.45 | Δ | ○ | X |
| 0.5 | X | Δ | Δ |
| 0.55 | X | X | Δ |

X: cell aggregation,
Δ: partial aggregation of cells (about 20~50%),
○: well stirred state As shown in Table 5, it could be confirmed that the reactor is stirred homogenously without cell aggregation by using 0.3 to 0.35 VVM of carbon dioxide in the reactor having a partition interval of 10 cm; the reactor is stirred homogenously without cell aggregation by using 0.35 to 0.45 VVM of carbon dioxide in the reactor having a partition interval of 15 cm. On the other hands, since the reactor is not stirred homogenously even using 0.1 to 0.45 VVM of carbon dioxide in the reactor having a partition interval of 25 cm, 0.5 VVM or more carbon dioxide should be fed for homogeneous stirring. However, at the time of feeding 0.5 VVM or more carbon dioxide, carbon dioxide of which the amount is more than the amount required for the growth of organisms is supplied, buffer is required for preventing a change in pH of a medium, and the amount of carbon dioxide to be discharged uselessly may be increased.

The experiment is carried out by using a sprayer having a diameter of 1.2 cm. Even though a sprayer with a larger diameter is used and a partition interval is increased, it is expected that the reactor is stirred homogeneously by bubble from the sprayer.

The present invention was described in detail with respect to the specific portion, but it is only a preferable embodiment in those skilled in the art and does not limit the scope of the present invention. Therefore, the substantial range of the present invention is defined by the accompanying claims and equivalent thereof.

What is claimed is:

1. A photobioreactor, consisting of:
   a reaction vessel having an inner space in which photosynthesis occurs by photosynthetic organisms;
   a multipurpose inlet/outlet detachably formed at the outside upper end of the reaction vessel, the multipurpose inlet/outlet comprising a nut-shaped fixing connection portion cap, a bolt-shaped fixing connection portion, and a stopping rubber, wherein the stopping rubber is disposed between the nut-shaped fixing connection portion cap and the bolt-shaped fixing connection portion when the nut-shaped fixing connection portion cap and the bolt-shaped fixing connection portion are combined with each other;
an outer pipe connected to the multipurpose inlet/outlet at the outside of the reaction vessel; and
an inner pipe connected to the multipurpose inlet/outlet at the inside of the reaction vessel,
wherein the reaction vessel is made of a transparent film, the transparent film consisting of a mixed film (PET+CPP) of polyethylene terephthalate (PET) and non-stretched polypropylene (CPP),
wherein the inner space of the reaction vessel is partially partitioned at interval of 3-30 cm by attaching the front and rear surfaces of the reaction vessel to each other in a vertical line forming a corrugated partition, the front and rear surfaces of the reaction vessel being directly attached to each other without interposing an intermediate member therebetween, the corrugated partition formed between the multipurpose inlet/outlet and the bottom of the reaction vessel, and
wherein the front and rear surfaces of the reaction vessel are attached to each other to form three vertical lines which are apart from each other such that the three vertical lines are apart from each other by a distance same as or smaller than 15 cm and a side surface length of the photobioreactor is 2 to 10 cm.

2. The photobioreactor of claim 1, wherein the reaction vessel includes, at the upper portion thereof, a hanging portion hanging the photobioreactor.

3. The photobioreactor of claim 1, wherein the multipurpose inlet/outlet includes a hole for injecting photosynthetic organisms, culture solution, and a carbon dioxide-containing gas, extracting a specimen sample, and discharging gas.

4. The photobioreactor of claim 3, wherein the outer pipe outside the reaction vessel is connected to the inner pipe inside the reaction vessel through the hole formed in the multipurpose inlet/outlet.

5. A photobioreactor, consisting of:
a reaction vessel having an inner space in which photosynthesis occurs by photosynthetic organisms;
a multipurpose inlet/outlet detachably formed at the outside upper end of the reaction vessel, the multipurpose inlet/outlet comprising a nut-shaped fixing connection portion cap, a bolt-shaped fixing connection portion, and a stopping rubber, wherein the stopping rubber is disposed between the nut-shaped fixing connection portion cap and the bolt-shaped fixing connection portion when the nut-shaped fixing connection portion cap and the bolt-shaped fixing connection portion are combined with each other;
an outer pipe connected to the multipurpose inlet/outlet at the outside of the reaction vessel;
an inner pipe connected to the multipurpose inlet/outlet at the inside of the reaction vessel; and
a sprayer attached to a bottom end of the inner pipe for dispersing carbon dioxide in the photobioreactor,
wherein the reaction vessel is made of a transparent film, the transparent film consisting of a mixed film (PET+CPP) of polyethylene terephthalate (PET) and non-stretched polypropylene (CPP),
wherein the inner space of the reaction vessel is partially partitioned at interval of 3-30 cm by attaching the front and rear surfaces of the reaction vessel to each other in a vertical line forming a corrugated partition, the front and rear surfaces of the reaction vessel being directly attached to each other without interposing an intermediate member therebetween, the corrugated partition formed between the multipurpose inlet/outlet and the bottom of the reaction vessel, and
wherein the front and rear surfaces of the reaction vessel are attached to each other to form three vertical lines which are apart from each other such that the three vertical lines are apart from each other by a distance same as or smaller than 15 cm and a side surface length of the photobioreactor is 2 to 10 cm.

6. The photobioreactor of claim 5, wherein the lower portion of the reaction vessel where the sprayer is located includes a groove in a "V" shape.

7. The photobioreactor of claim 6, wherein the groove in a "V" shape has an internal angle from 30 to 160°.

8. The photobioreactor of claim 6, wherein the number of grooves in a "V" shape has the same as the number of sprayers.

9. The photobioreactor of claim 5, wherein no port is formed in the groove in a "V" shape of the lower portion of the reaction vessel.

10. The photobioreactor of claim 1, wherein:
a bottom side of the reaction vessel is shaped to include a plurality of V-shaped grooves; and
no opening is formed in each of the V-shaped grooves of the bottom side of the reaction vessel.

11. The photobioreactor of claim 1, wherein:
a bottom side of the reaction vessel is shaped to include a plurality of V-shaped grooves; and
no opening is formed in each of the V-shaped grooves of the bottom side of the reaction vessel.

* * * * *